United States Patent
Bahl et al.

(10) Patent No.: US 6,723,502 B2
(45) Date of Patent: Apr. 20, 2004

(54) HEPATITIS C ANTIGEN—ANTIBODY COMBINATION ASSAY FOR THE EARLY DETECTION OF INFECTION

(76) Inventors: Chander Bahl, 5 Jenny Jump Ct., Flemington, NJ (US) 08822; Patrick Niven, 2 Lamar Dr., Denville, NJ (US) 07834; Antonio Samson, 15 Intervale Rd., Livingston, NJ (US) 07039; Denise Madjor, 104 Winding Way, Yardville, NJ (US) 08620

( * ) Notice: Subject to any disclaimer, the term of this patent is extended or adjusted under 35 U.S.C. 154(b) by 0 days.

(21) Appl. No.: 10/108,610

(22) Filed: Mar. 28, 2002

(65) Prior Publication Data

US 2003/0049608 A1 Mar. 13, 2003

Related U.S. Application Data

(60) Provisional application No. 60/279,276, filed on Mar. 28, 2001.

(51) Int. Cl.[7] .......................... C12Q 1/70; G01N 33/576
(52) U.S. Cl. ............................................. 435/5; 436/518
(58) Field of Search ............................... 435/5; 436/518

(56) References Cited

U.S. PATENT DOCUMENTS 5,616,460 A * 4/1997 Figard ........................... 435/5

2002/0173493 A1 * 11/2002 Aoyagi et al.
2002/0192639 A1 * 12/2002 Chien et al.

FOREIGN PATENT DOCUMENTS

EP           1 020 727 A        7/2000

OTHER PUBLICATIONS

Aoyagi et al., Development of a Simple and HIghly Sensitive Immunoassay for Hepatitis C Core Antigen. Journal of Clinical Microbiology 37(6):1802–1808, 1999.*
The Merck Index, Eleventh Edition, Budavari et al., Eds. 1989, Monograph 6681.*
Lee, S.R. et al., "Efficacy of a hepatitis C virus core antigen enzyme–linked immunosorbent assay for the identification of 'window–phase' blood donations", Vox Sanguinis, vol. 80, pp. 19–23, Jan. 2001, XP02210662.
Courouce AM et al., "Efficacy of HCV core antigen detection during the preseroconversion period", Transfusion, vol. 40, pp. 1198–1202, Oct. 2000, XP002210663.
European Search Report, dated Sep. 16, 2002, for European Appln. No. EP 02252195.

* cited by examiner

*Primary Examiner*—Donna C. Wortman

(57) ABSTRACT

Described herein is an ELISA based assay for the detection of HCV infection. This new assay can detect HCV infection earlier than the currently used assays for the screening of blood for HCV infection by using a combination of HCV antigens and anti-core antibodies to capture HCV.

2 Claims, No Drawings

HEPATITIS C ANTIGEN— ANTIBODY COMBINATION ASSAY FOR THE EARLY DETECTION OF INFECTION

This application claims the benefit of U.S. provisional application No. 60/279,276 filed Mar. 28, 2001.

BACKGROUND OF THE INVENTION

An estimated 170 million people worldwide have been infected by hepatitis C virus (HCV). In the next few years, the number of U.S. deaths for HCV-caused liver disease and cancer may overtake deaths caused by Acquired Immune Deficiency Syndrome (AIDS).

The transmission of HCV seems to require blood-to-blood contact. Carrying a single strand of ribonucleic acid (RNA), HCV contains just one gene, coding for a polyprotein that is subsequently spliced into at least 10 functional proteins. Clearly, the ability to test the blood supply for HCV is of great importance. Furthermore, the earlier the stage of HCV one can detect, the better.

Therefore, we have developed an ELISA based assay for the detection of HCV infection. This new assay can detect HCV infection earlier than the currently used assays for the screening of blood for HCV infection. Current assays are based on the detection of anti-HCV antibodies in infected blood by capturing these antibodies by HCV protein sequences represented by recombinant proteins or peptides.

For example, the Ortho HCV 3.0 ELISA uses multiple antigens to detect anti-HCV antibodies very early in seroconversion. However, there is a significant window period in viremic individuals before they develop anti-HCV antibodies. This window period can be as long as 60 days. During this period the individual, though highly infective, will go undetected by current HCV screening assays.

SUMMARY OF THE INVENTION

One object of the invention is to provide a diagnostic test that can detect HCV infection during the window period described above by capturing both HCV core antigen and antibodies. We describe herein a method for detecting HCV infection earlier than the currently used antibodies assays. This has been accomplished by providing a test that detects HCV core antigen in addition to the anti-HCV antibodies.

Another object of the invention is to provide a method for determining the presence of HCV in a sample, comprising, contacting the sample with HCV antigens and anti-HCV core antibodies attached to a solid phase, adding a polyoxyethylene ether to said sample, detecting captured antigens and antibodies by adding labeled anti-human IgG and labeled anti-HCV core antibodies and detecting the signal as an indication of the presence of HCV infection.

Another object of the invention is to provide certain detergents that are needed to release the HCV core antigen from the virus by disrupting the envelope protein and/or the lipid layer.

DETAILED DESCRIPTION OF THE INVENTION

It is preferrable in a combination assay for the detergents to release the core antigen from the virus and yet not have a negative impact on the ability of the HCV recombinant proteins to capture anti-HCV antibodies. In a preferred embodiment of the invention, detergents from the polyoxyethylene ethers class are used for this purpose. Commonly available detergents in this class are: BRIJ 30, BRIJ 35, 56, 58, 92, 96, 98, 700 and MYRJ 52, 59, 53, 45. These detergents help in releasing the HCV core antigen from the virus but the presence of these detergents do not negatively impact the anti-HCV assay Certain detergents can effect the antibody detection by either affecting the recombinant antigens coated on the solid phase or inactivating the anti-HCV antibodies in the sample. Some of the detergents like N-Lauryl Sarcosine used in the detection of HCV core assay destroy the ability of HCV recombinant proteins c22-3, c200 and NS5 to detect anti HCV antibodies in Ortho HCV 3.0 ELISA.

As used herein a "sample" refers to any substance which may contain the analyte of interest. A sample can be biological fluid, such as whole blood or whole blood components including red blood cells, white blood cells, platelets, serum and plasma, ascites, urine, cerebrospinal fluid, and other constituents of the body which may contain the analyte of interest.

As used herein "antigen" rerers to any antigenic substance including recombinant proteins and peptides or a mixture thereof.

EXAMPLE

The following examples demonstrate the advantages and utility of the invention by describing a list of detergents evaluated and the results obtained by using the above described assay. One skilled in the art would recognize that the detection of HCV antibody and antigen can be done separately or simultaneously. These examples are meant to illustrate, but not limit, the spirit and scope of the invention.

Example 1

An Antigen-Antibody Combination Assay

HCV antigens c200-3, NS-5 and a modified core antigen C22KSN 47, 48 or c22KSR47L along with two anti-core monoclonal antibodies (anti core murine monoclonals Pep10, 12) were coated onto microwells in phosphate buffer. Antigens were modified by modifying the DNA clones coding for the recombinant proteins c22-3 containing the HCV1 sequence. These procedures involve site directed mutagenesis using synthetic oligonucleotides (Sambrook, Fritsh and Maniatis in Molecular Cloning, A laboratory manual, second edition, Cold Spring Harbor Press, Chapter 15, 1989). After overnight incubation the buffer containing the coating proteins was removed and the microwells washed with phosphate buffered saline containing a detergent Tween 20. The antigen/antibody coated microwells were then treated with BSA/sucrose solution to block all of the protein binding sites on the microwells. After 2–24 hours the BSA/sucrose solution was removed and the microwells air dried and stored under a descicant.

Example 2

100 mL of sample to be tested was diluted into 100 mL of PBS solution containing bovine serum albumin, superoxide dismutase, yeast extract and 1% Brij 58 or Brij 35 or a mixture of both. The diluted specimens were pipetted into HCV antigen/monoclonal antibodies coated microwells (as described in Example 1). These microwells were incubated at 37° C. for 90 minutes. The microwells were then washed 5 times with PBS containing 0.5% Tween 20. A 200 mL solution of a murine anti-human IgG labeled with horseradish peroxidase (HRP) and an anti-HCV core monoclonal antibody (Anti Pep4) labeled with HRP was added. After an incubation of 30 minutes the microwells were washed 5 times with PBS Tween 20. A solution of orthophenylenediamine and hydrogen peroxide was added to each well. After incubation in the dark for 30 minutes the reaction was stopped by adding 50 microliters of 4N sulfuric acid. The plates were read at 495 nM. An orange color in either well indicates that the specimen being tested is infected with HCV.

Example 3

Effects of Polyoxyethylene Ethers on HCV Antibody or Antigen Assays

Effect of the addition of various polyoxyethylene ethers on the HCV 3.0 anti-HCV assay or HCV core antigen ELISA assay is shown below in Tables 1A and 1B. In the HCV core antigen ELISA assay N-Lauryl sarcosine used in the commercial HCV core antigen was replaced by different concentrations of detergents in column one. In the HCV 3.0 anti-HCV assay the detergents were added to the specimen diluent used in the HCV 3.0 assay.

TABLE 1A

| Detergent Tested | | | HCV 3.0 Ab ELISA | | | | | |
|---|---|---|---|---|---|---|---|---|
| | | | Base Matrix | | | HCV Antibody Reactive | | |
| | | | 0.25% | 0.125% | 0.06% | 0.25% | 0.125% | 0.06% |
| | | SYN. | 0.125% | 0.06% | 0.03% | 0.125% | 0.06% | 0.03% |
| polyoxyethylene | 2 oleyl ether | Brij 92 | 0.056 | 0.035 | 0.041 | 1.543 | 1.432 | 1.405 |
| polyoxyethylene | 8 stearate | Myrj 45 | 0.019 | 0.024 | 0.025 | 1.208 | 1.286 | 1.313 |
| polyoxyethylene | 5 lauryl ether | | 0.033 | 0.046 | 0.058 | 1.168 | 1.274 | 1.351 |
| polyoxyethylene | 50 stearate | Myrj 53 | 0.044 | 0.069 | 0.083 | 1.368 | 1.361 | 1.262 |
| polyoxyethylene | 8 lauryl ether | | 0.064 | 0.070 | 0.059 | 1.223 | 1.219 | 1.277 |
| polyoxyethylene | 9 lauryl ether | | 0.057 | 0.055 | 0.061 | 1.312 | 1.260 | 1.225 |
| polyoxyethylene | 10 lauryl ether | | 0.049 | 0.059 | 0.064 | 1.192 | 1.069 | 1.161 |
| polyoxyethylene | 10 cetyl ether | Brij 56 | 0.053 | 0.093 | 0.059 | 0.994 | 1.212 | 1.209 |
| polyoxyethylene | 10 oleyl ether | Brij 97 | 0.031 | 0.056 | 0.072 | 1.316 | 1.341 | 1.534 |
| polyoxyethylene | 100 stearate | Myrj 59 | 0.047 | 0.050 | 0.045 | 1.751 | 1.615 | 1.418 |
| polyoxyethylene | 20 cetyl ether | Brij 58 | 0.058 | 0.046 | 0.062 | 1.568 | 1.507 | 1.488 |
| polyoxyethylene | 40 stearate | Myrj 52 | 0.048 | 0.063 | 0.067 | 1.502 | 1.308 | 1.194 |
| polyoxyethylene | 100 stearyl ether | Brij 700 | 0.043 | 0.045 | 0.052 | 1.600 | 1.482 | 1.503 |
| polyoxyethylene | 20 oleyl ether | Brij 98 | 0.053 | 0.044 | 0.050 | 1.632 | 1.542 | 1.493 |
| polyoxyethylene | 23 lauryl ether | Brij 35 | 0.067 | 0.055 | 0.065 | 1.492 | 1.415 | 1.473 |
| polyoxyethylene | 7 lauryl ether | | 0.065 | 0.105 | 0.100 | 1.151 | 1.458 | 1.497 |
| polyoxyethylene | 4 lauryl ether | Brij 30 | 0.093 | 0.058 | 0.185 | 0.867 | 1.135 | 1.190 |
| polyoxyethylene | 3 lauryl ether | | 0.035 | 0.042 | 0.075 | 0.995 | 0.927 | 1.156 |
| Pluronic F-127 | | | 0.025 | 0.030 | 0.035 | 1.521 | 1.327 | 1.271 |
| Control | | | 0.075 (3.0 SD) | | | 1.358 (3.0 SD) | | |

TABLE 1B

| Detergent Tested | | | HCV Antigen Protoype | | | | | |
|---|---|---|---|---|---|---|---|---|
| | | | Base Matrix | | | HCV Antigen Reactive | | |
| | | | 0.25% | 0.125% | 0.06% | 0.25% | 0.125% | 0.06% |
| | | SYN. | 0.125% | 0.06% | 0.03% | 0.125% | 0.06% | 0.03% |
| polyoxyethylene | 2 oleyl ether | Brij 92 | 0.010 | 0.010 | 0.032 | 0.609 | 0.847 | 0.502 |
| polyoxyethylene | 8 stearate | Myrj 45 | 0.028 | 0.021 | 0.022 | 0.880 | 0.509 | 0.433 |
| polyoxyethylene | 5 lauryl ether | | 0.002 | 0.004 | 0.007 | 0.195 | 0.243 | 0.265 |
| polyoxyethylene | 50 stearate | Myrj 53 | 0.014 | 0.040 | 0.006 | 0.573 | 0.536 | 0.659 |
| polyoxyethylene | 8 lauryl ether | | 0.009 | 0.010 | 0.014 | 0.326 | 0.384 | 0.343 |
| polyoxyethylene | 9 lauryl ether | | 0.008 | 0.008 | 0.005 | 0.360 | 0.379 | 0.212 |
| polyoxyethylene | 10 lauryl ether | | 0.010 | 0.013 | 0.020 | 0.495 | 0.556 | 0.344 |
| polyoxyethylene | 10 cetyl ether | Brij 56 | 0.004 | 0.001 | 0.016 | 0.445 | 0.298 | 0.390 |
| polyoxyethylene | 10 oleyl ether | Brij 97 | 0.004 | 0.006 | 0.021 | 0.371 | 0.419 | 0.479 |
| polyoxyethylene | 100 stearate | Myrj 59 | 0.019 | 0.021 | 0.023 | 0.429 | 0.320 | 0.369 |
| polyoxyethylene | 20 cetyl ether | Brij 58 | 0.008 | 0.011 | 0.028 | 0.546 | 0.898 | 0.564 |
| polyoxyethylene | 40 stearate | Myrj 52 | 0.009 | 0.005 | 0.006 | 0.579 | 0.412 | 0.661 |
| polyoxyethylene | 100 stearyl ether | Brij 700 | 0.016 | 0.023 | 0.019 | 0.294 | 0.307 | 0.319 |
| polyoxyethylene | 20 oleyl ether | Brij 98 | 0.008 | 0.011 | 0.032 | 0.557 | 0.718 | 0.539 |
| polyoxyethylene | 23 lauryl ether | Brij 35 | 0.022 | 0.028 | 0.029 | 0.722 | 0.494 | 0.309 |
| polyoxyethylene | 7 lauryl ether | | 0.009 | 0.009 | 0.016 | 0.228 | 0.289 | 0.309 |
| polyoxyethylene | 4 lauryl ether | Brij 30 | −0.001 | 0.001 | 0.008 | 0.194 | 0.158 | 0.212 |
| polyoxyethylene | 3 lauryl ether | | 0.004 | 0.005 | 0.013 | 0.106 | 0.168 | 0.162 |
| Pluronic F-127 | | | 0.013 | 0.013 | 0.012 | 0.324 | 0.285 | 0.268 |
| Control | | | 0.001 (nLs) | | | 1.109 (nLs) | | |

Example 4

Detection of HCV Core Antigen and/or Anti-HCV Antibodies

Detection of HCV core antigen or anti-HCV antibodies on plates coated with anti-core monoclonal antibodies c11-3 and c11-7 and HCV antigens c200-3, NS5 and a modified core antigen. (SOD fused protein containing core sequences aa10–99 with aa 47 and 48 deleted (c22KS(∇47–48). The specimens used were 4 sequential bleeds from a commercially available seroconversion panel. Core antigen was detected using c11-4 monoclonal antibody labeled with HRP, anti-HCV antibodies were detected by anti-human IgG labeled with HRP. By using the two antibodies together a cumulative signal was produced, as shown in the column labeled combo in Table 2.

TABLE 2

| SAMPLE | ANTI IgG | ANTI HCV CORE | COMBO |
|---|---|---|---|
| NEG MEAN* | 0.045 | 0.036 | 0.094 |
| BCP 6215 1 | 0.007 | 0.135 | 0.193 |
| BCP 6215 2 | 0.009 | 0.157 | 0.191 |
| BCP 6215 3 | 0.014 | 0.231 | 0.270 |
| BCP 6215 4 | 0.494 | 0.197 | 0.614 |

*signal obtained by using HCV negative samples

Example 5

Detection of HCV Core Antigen and/or Anti-HCV Antibodies

Detection of HCV core antigen and/or anti-HCV antibodies on plates coated with anti-core monoclonal antibodies c11-3 and c11-7 and HCV antigens c200-3, NS5 and a modified core antigen. (SOD fused protein containing core sequences aa10–99 with arginine at position 47 replaced with a leucine (c22KS (R47L)). The specimens used were 4 sequential bleeds from a commercially available seroconversion panel. Core antigen was detected using c11-4 monoclonal antibody labeled with HRP, anti-HCV antibodies were detected by anti-human IgG labeled with HRP. In the combo assay the two detecting antibodies, anti core monoclonal and anti-human IgG monoclonal antibody labeled with HRP were used as a mixture.

TABLE 3

| SAMPLE | ANTI IgG | ANTI HCV CORE | COMBO |
|---|---|---|---|
| NEG MEAN | 0.045 | 0.036 | 0.094 |
| BCP 6215 1 | 0.007 | 0.135 | 0.193 |
| BCP 6215 2 | 0.009 | 0.157 | 0.191 |
| BCP 6215 3 | 0.014 | 0.231 | 0.270 |
| BCP 6215 4 | 0.494 | 0.197 | 0.614 |

Example 6

Anti-IgG Comparison

A comparison of anti-HCV reactivity of seroconverter panel in microwells coated with two different HCV core proteins is shown in Table 4.

TABLE 4

| SAMPLE | SOD/c22KS (Δ47–48) | SOD/c22KS (R47L) |
|---|---|---|
| NEG MEAN | 0.045 | 0.076 |
| BCP 6215 1 | 0.007 | 0.015 |
| BCP 6215 2 | 0.009 | 0.021 |

TABLE 4-continued

| SAMPLE | SOD/c22KS (Δ47–48) | SOD/c22KS (R47L) |
|---|---|---|
| BCP 6215 3 | 0.014 | 0.028 |
| BCP 6215 4 | 0.494 | 0.498 |

Example 7

Comparison of core antigen detection of seroconverter panel in microwells coated with two different core antigens is shown in Table 5.

TABLE 5

| | Anti-HCV Core Comparison | |
|---|---|---|
| SAMPLE | SOD/c22KS (Δ47–48) | SOD/c22KS (R47L) |
| NEG MEAN | 0.036 | 0.047 |
| BCP 6215 1 | 0.135 | 0.224 |
| BCP 6215 2 | 0.157 | 0.189 |
| BCP 6215 3 | 0.231 | 0.304 |
| BCP 6215 4 | 0.197 | 0.189 |

Example 8

Comparison of combo reactivity of seroconverter panel in microwells coated with two different core antigens is shown in Table 6.

TABLE 6

| | HCV Combo Comparison | |
|---|---|---|
| SAMPLE | SOD/c22KS (Δ47–48) | SOD/c22KS (R47L) |
| NEG MEAN | 0.094 | 0.144 |
| BCP 6215 1 | 0.193 | 0.247 |
| BCP 6215 2 | 0.191 | 0.226 |
| BCP 6215 3 | 0.270 | 0.328 |
| BCP 6215 4 | 0.614 | 0.658 |

We claim:

1. A method for determining the presence of HCV in a sample, consisting essentially of:
    contacting the sample with HCV antigens and anti-HCV core antibodies attached to a solid phase, adding a polyoxyethylene ether to said sample, detecting captured antigens and antibodies by adding labeled anti-human IgG and labeled anti-HCV core antibodies and detecting the signal as an indication of the presence of HCV infection,
    wherein the polyoxyethylene ether is selected from the group consisting of 2 oleyl ether, 8 stearate, 50 stearate, 3 lauryl ether, 4 lauryl ether, 5 lauryl ether, 7 lauryl ether, 8 lauryl ether, 9 lauryl ether, 10 lauryl ether, 10 cetyl ether, 10 oleyl ether, 100 stearate, 20 cetyl ether, 40 stearate, 100 stearyl ether, 20 oleyl ether, 23 lauryl ether, and combinations thereof.

2. An immunoassay kit, suitable for detecting the presence of HCV in a sample, consisting essentially of amounts sufficient to perform said immunoassay of:
    (a) HCV capture antigens and antibodies bound to a solid phase,
    (b) detectably labeled anti-HCV core antibodies, and
    (c) a polyoxyethylene ether selected from the group consisting of 2 oleyl ether, 8 stearate, 50 stearate, 3 lauryl ether, 4 lauryl ether, 5 lauryl ether, 7 lauryl ether, 8 lauryl ether, 9 lauryl ether, 10 lauryl ether, 10 cetyl ether, 10 oleyl ether, 100 stearate, 20 cetyl ether, 40 stearate, 100 stearyl ether, 20 oleyl ether, 23 lauryl ether, and combinations thereof.

* * * * *